US007846947B2

(12) United States Patent
Siebert et al.

(10) Patent No.: US 7,846,947 B2
(45) Date of Patent: Dec. 7, 2010

(54) USE OF OCTENIDINE DIHYDROCHLORIDE IN SEMISOLID PREPARATIONS

(75) Inventors: Jorg Siebert, Norderstedt (DE); Mona Golombiewski, Lüneburg (DE); Rita Blankenburg, Hamburg (DE); Peter Goroncy-Bermes, Hamburg (DE); Andreas Dettmann, Hamburg (DE); Sabine Behrends, Appen (DE)

(73) Assignee: Air Liquide Sante (International), Paris (FR)

( * ) Notice: Subject to any disclaimer, the term of this patent is extended or adjusted under 35 U.S.C. 154(b) by 0 days.

(21) Appl. No.: 12/066,832

(22) PCT Filed: Sep. 12, 2006

(86) PCT No.: PCT/EP2006/066283

§ 371 (c)(1),
(2), (4) Date: May 15, 2008

(87) PCT Pub. No.: WO2007/031520

PCT Pub. Date: Mar. 22, 2007

(65) Prior Publication Data

US 2008/0221165 A1  Sep. 11, 2008

(30) Foreign Application Priority Data

Sep. 15, 2005  (DE)  ........................ 10 2005 045 145

(51) Int. Cl.
*A61K 31/444* (2006.01)
*A61P 17/02* (2006.01)
*A61P 17/00* (2006.01)
*A61P 17/10* (2006.01)
*A01N 25/04* (2006.01)

(52) U.S. Cl. ...................... 514/332; 514/944; 514/967; 424/404; 424/405; 424/422; 424/430

(58) Field of Classification Search ................. 514/332, 514/944, 967; 424/404, 405, 422, 430
See application file for complete search history.

(56) References Cited

U.S. PATENT DOCUMENTS

| | | | | |
|---|---|---|---|---|
| 4,614,649 A | * | 9/1986 | Gorman et al. | 424/54 |
| 5,176,901 A | * | 1/1993 | Gallopo et al. | 424/54 |
| 6,380,391 B2 | * | 4/2002 | Beilfuss et al. | 546/255 |

FOREIGN PATENT DOCUMENTS

| | | |
|---|---|---|
| DE | 27 08 331 A1 | 9/1977 |
| DE | 39 25 540 C1 | 8/1990 |
| WO | WO 0202128 | 1/2002 |
| WO | 2006/099359 A2 | 9/2006 |

OTHER PUBLICATIONS

Remington's Pharmaceutical Sciences, 15th Edition, 1975, Mack Publishing Company, p. 1244.*
Sedlock et al., "Microbicidal Acitivity of Octenidine Hydrochloride, a New Alkanediylbis[Pyridine] Germicidal Agent," Antimicrobial Agents & Chemotherapy, vol. 28, No. 6, pp. 786-790 (1985).
Friese et al., "Topical antiseptics as an alternative in the treatment of acule vulvovaginal candidosis," Arc. of Gyn. & Obst., vol. 268, No. 3, pp. 194-197 (Aug. 2003).

* cited by examiner

*Primary Examiner*—Yvonne L Eyler
*Assistant Examiner*—Donna Jagoe
(74) *Attorney, Agent, or Firm*—Young & Thompson

(57) ABSTRACT

The invention relates to the use of octenidine dihydrochloride for manufacturing a semisolid pharmaceutical composition for the treatment of wounds, atopic dermatitides, infected eczemas, dermatomycoses, vaginal infections, acne, herpes and/or for controlling multidrug-resistant pathogens, where the composition comprises from 0.005 to 5% by weight octenidine dihydrochloride, and a corresponding composition.

7 Claims, No Drawings

USE OF OCTENIDINE DIHYDROCHLORIDE IN SEMISOLID PREPARATIONS

This application is a 371 of PCT/EP2006/066283 filed Sep. 12, 2006 which claims priority to German Application Number 102005045145.4 filed Sep. 15, 2005.

The present invention relates to the use of octenidine dihydrochloride for manufacturing a semisolid pharmaceutical composition for the treatment of wounds, atopic dermatitides, infected eczemas, dermatomycoses, vaginal infections, acne, herpes and/or for controlling multidrug-resistant pathogens.

The use of semisolid pharmaceutical compositions for the treatment of wounds, infected eczemas, dermatomycoses, vaginal infections, acne, herpes and/or for controlling multidrug-resistant pathogens is known. State of the art for the treatment of atopic dermatitides and infected eczemas is for example the use of antibiotics and bufexamac, which are known to lead to the development of resistance. Development of resistance is enhanced on frequent use of antibiotics, and the well-known MRSA problems arise. Imidazoles (e.g. clotrimazole) are used for the treatment of dermatomycoses but often lead to the development of recurrences. Products employed for the treatment of vaginal infections are those specifically for vaginal mycoses (in these cases too once again the abovementioned imidazoles with the described disadvantages) or products specifically for bacterial infections (for example PVP-iodine with the disadvantage of soiling of underclothes). State of the art in the treatment of acne are antibiotics (e.g. erythromycin, neomycin, tetracyclines, disadvantage: risk of development of resistance), benzoyl peroxide (disadvantage: skin irritation, drying of the skin), tretinoin (vitamin A acid, disadvantage: skin irritation) and further active ingredients such as salicylic acid, sulphur or resorcinol, which have disadvantages as the result of insufficient tolerability. The virustatics (e.g. acyclovir) used to date for the treatment of herpes show incompatibilities with skin in the form of reddening and scaling. Antibiotics have been used to date for the treatment of multidrug-resistant pathogens (e.g. MRSA) but, as described above, lead to the development of resistance.

Known semisolid products with antimicrobial active ingredients are thus associated with numerous disadvantages, inter alia:
- development of resistance (e.g. antibiotics),
- intense intrinsic colour of the product, which is frequently not accepted by users (PVP-iodine, dyes with antimicrobial activity, such as gentian violet and brilliant green),
- toxicological unacceptability
- limited range of action (e.g. triclosan).

It was therefore an object of the invention to provide pharmaceutical compositions which do not have these disadvantages, are active against a large number of microbes, can be formulated with a large number of formulation bases for pharmaceutical compositions, and are suitable for the treatment of wounds, atopic dermatitides, infected eczemas, dermatomycoses, vaginal infections, acne, herpes and/or for controlling multidrug-resistant pathogens. It is particularly intended that the compositions be toxicologically acceptable and not prone to the development of resistance.

It has now surprisingly been found that this object is achieved by the use of octenidine dihydrochloride for manufacturing a semisolid pharmaceutical composition for the treatment of wounds, atopic dermatitides, infected eczemas, dermatomycoses, vaginal infections, acne, herpes and/or for controlling multidrug-resistant pathogens, where the composition comprises from 0.005 to 5% by weight octenidine dihydrochloride. The invention further relates to semisolid pharmaceutical compositions having a content of from 0.005 to 5% by weight octenidine dihydrochloride for the treatment of wounds, infected eczemas, dermatomycoses, vaginal infections, acne, and/or for controlling multidrug-resistant pathogens. The term "semisolid" in this connection refers to all dosage forms which are not solid (tablets, capsules) and not liquid (drops, syrups).

Semisolid Pharmaceutical Forms

Ointments (lat. unguenta) are spreadable preparations which are intended for use on the skin by application or rubbing in. They consist of one or more ointment bases (such as petrolatum, wool fat, lanolin etc.) into which the active ingredient is incorporated. The active ingredient should be dissolved or very finely dispersed. In order to increase the solubility, ointments often comprise water or oils. However, the fat/oil content in an ointment is higher than the water content.

Creams are very similar to ointments but the water content therein is higher than the fat/oil content.

CreSa is a short designation for a combination of cream and ointment.

The viscosity of ointments and creams according to the invention is generally from 500 to 15 000 mPa·s, preferably 1000 to 10 000 mPa·s, measured with a rotational viscometer at 95 $s^{-1}$ and 20° C. (e.g. of the RV20 type, M5 system, SV1 measuring unit, from Thermo Haake).

Paste is the designation for ointments in which ingredients in powder form (e.g. zinc oxide, talc etc.) are dispersed in large amount. Pastes comprise no water and, through the large proportion of powders, are substantially firmer than ointments.

Hydroalcoholic gels (hydrogels) are valued for their transparency and non-greasy characteristics. Lipophilic gels (oleogels) are likewise employed because of their aesthetic appearance and their consistency-conferring properties. Gels are predominantly intended for external use and should be applied thinly.

A hydrogel is a usually translucent composition which is manufactured with the aid of gelatin, tragacanth, Carbopol or similar swelling agents with the addition of water and glycerol. They have a cooling effect through the evaporation of the water.

Lipophilic gels include a lipophilic phase. Matrix formers employed, besides higher-molecular weight homologues of the lipid phase, are also organo-modified bentonites (Benton®) and colloidal silicon dioxide.

Emulsion means preparations consisting of immiscible liquids, e.g. oil and water. A distinction is made between W/O (water in oil) or O/W (oil in water) emulsions and ambiphilic emulsions. The latter must be vigorously shaken before use. Addition of an emulsifier makes it possible for the lipids to be distributed extremely finely within one another, and the emulsions are thus stable, i.e. the oil and the water do not separate again. Depending on the mode of application, emulsions are intended for internal or external use. Emulsions for external use are frequently referred to as lotions. This takes the form of an oil-in-water emulsion.

CreLo means a combination of cream and lotion.

Suppositories (lat. suppositoria) are single-dose pharmaceutical preparations which have various shapes and are intended for introduction into the rectum and there deliver the active ingredient after melting or dissolving. They consist of a hard fat (e.g. Stadimol) or polyethylene glycol, in which the active ingredient is incorporated with input of heat. This heated composition is then poured into moulds. Hard fat suppositories are heat-sensitive and should therefore never be stored above 25° C. A normal suppository size for adults is about 2 g and for children about 1 g. Suppositories should best be introduced after defecation and in supine position. Introduction can be facilitated by previously dipping the suppository in water. Rubbing in creams or ointments should be avoided because it may impair the activity of the suppositories.

Suppositories to be introduced into the vagina are differentiated into vaginal suppositories and vaginal pessaries (lat. ovulum). The vaginal suppositories are similar in manufacture and basic composition to the "normal" suppositories. Vaginal pessaries mostly consist of gelatin, water and glycerol and have a spherical shape. The weight of both dosage forms is about 3 g. Application should take place where possible in the evening and in the supine position. In this case too, creams should be dispensed with for the introduction. An introduction aid is supplied by the manufacturer together with various suppositories. Storage below 25° C. is important here too.

Octenidine dihydrochloride corresponds to the following formula:

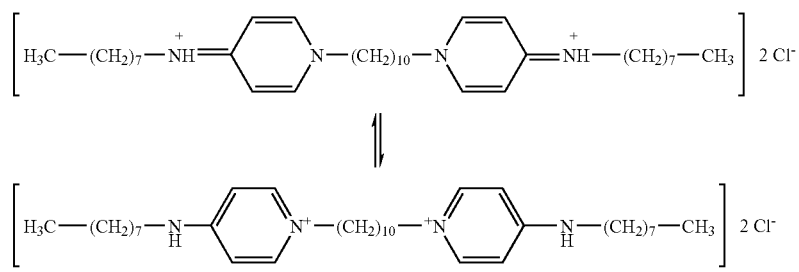

The active ingredient has been employed for many years in a mucosal and wound antiseptic in the form of an aqueous solution (cf. the product Octenisept® of Schülke & Mayr GmbH, Norderstedt, Germany). This administration form does, however, restrict the use for some indications. If the product is for therapeutic reasons to remain for a lengthy period on the surface to be treated (e.g. skin or mucosa), the preparation must be spreadable. It was, however, surprising that it is possible with octenidine dihydrochloride as active ingredient to formulate a wide diversity of semisolid pharmaceutical compositions, it being necessary to ensure good tolerability through the choice of the ingredients in agreement with the respective indication.

In a preferred embodiment, the composition comprises from 0.01 to 2% by weight octenidine dihydrochloride, preferably from 0.02 to 1% by weight, more preferably from 0.03 to 0.8% by weight, in particular from 0.05 to 0.5% by weight.

The composition is preferably in the form of a gel, O/W cream, W/O cream, O/W/O cream, W/O/W cream, ambiphilic cream, ointment or suppository. A preferred embodiment in this connection is one where the composition is formulated as compositions which can be used topically (externally) or rectally or vaginally.

It is possible according to the invention for the composition to comprise further active ingredients which supplement the activity of octenidine dihydrochloride and can where appropriate be employed in a distinctly lower concentration than in known commercial products when they are combined with octenidine dihydrochloride. It is thus possible in some cases to reduce distinctly the relevant disadvantages. These further active ingredients include: clotrimazole and other antimycotics with local activity, cortisones, tretinoin, benzoyl peroxide, acyclovir, local anaesthetics (e.g. benzocaine, lidocaine, polidocanol inter alia), antibiotics, bufexamac, etc.

1. Wound Treatment

In a first embodiment, the preparation according to the invention is employed for the treatment of wounds. This entails preferably choosing an emulsifier-free formulation which comprises a large extent of moisture factors (e.g. a gel).

2. Atopic Dermatitides and Infected Eczemas

A formulation of a preparation comprising octenidine dihydrochloride for use according to the invention for the treatment of infected eczemas is preferably, according to skin type, an oil-in-water (O/W), water-in-oil (W/O) or ambiphilic emulsion (creams).

3. Dermatomycoses

Gels and creams are preferably used as formulation for the semisolid preparation for the treatment of mycoses.

4. Vaginal Infections

Dosage forms suitable and preferred for the treatment of vaginal infections are creams and suppositories. Octenidine dihydrochloride in preparations of these types displays a particularly advantageous effect because it is active both against fungi and against bacteria, and the use of two different products is unnecessary.

The advantages of the invention are evident in particular from the following examples.

EXAMPLE 1

Fucidin Cream (Comparative)

1 ml comprises: fusidic acid (antibiotic) 19.72 mg, further ingredients: cetyl alcohol, butylated hydroxyanisole, glycerol, potassium sorbate, polysorbate 60, hydrochloric acid, petrolatum, water.

The following formulations according to the invention were manufactured:

1. Gel 0.05 g octenidine dihydrochloride 9.90 g propylene glycol 2.50 g hydroxyethylcellulose water ad 100.00 g The viscosity of such gels is generally about 4500 to 5500 mPa·s (RS600 rotational viscometer, Z40 DIN Ti sensor, from Thermo Haake, at 34 s$^{-1}$, 20° C.).

2. Ointment
   0.2 g octenidine dihydrochloride
   6.0 g wool wax alcohols (mixture of sterols and higher aliphatic alcohols from wool wax, 33.5% by weight cholesterol)
   0.5 g cetylstearyl alcohol
   3.0 g liquid paraffin
   white petrolatum ad 100.00 g 3. O/W cream
   0.1 g octenidine dihydrochloride
   4.0 g glycerol monostearate 40-50
   6.0 g cetyl alcohol
   7.5 g medium-chain triglycerides (at least 95% by weight saturated fatty acids with 8 to 10 carbon atoms)
   25.5 g white petrolatum
   7.0 g macrogol 1000 glycerol monostearate
   The viscosity of such creams is in the range of about 5000 to 6500 mPa·s (RV20 rotational viscometer, M5 system, SV1 measuring unit, from Thermo Haake, at 95 s$^{-1}$, 20° C.).

4. W/O cream
   0.50 g octenidine dihydrochloride
   4.00 g Lameform TGI (triglycerol diisostearate)
   2.00 g Monomuls 90-018 (glycerol oleate)
   3.00 g beeswax, white
   2.00 g zinc stearate
   10.00 g Eutanol G (2-octyldodecanol)
   10.00 g isopropyl myristate
   5.00 g glycerol 85% by weight
   1.00 g Mg sulphate
   water ad 100.00 g 5. W/O cream
   0.30 g octenidine dihydrochloride
   2.63 g Monomuls 90-018
   2.11 g beeswax, white
   2.11 g zinc stearate
   3.16 g glycerol 85% by weight
   0.74 g Mg sulphate
   5.26 g low-viscosity paraffin
   10.53 g Cetiol V (decyl oleate)
   water ad 100.00 g 6. Antimycotic Gel
   0.1 g octenidine dihydrochloride
   0.5 g clotrimazole
   30.6 g 1-propanol
   10.0 g Dehyton K (cocoamidopropylbetaine)
   2.5 g Natrosol 250 HHX Pharm, Tylose H 100 000 p (hydroxyethylcellulose)
   water ad 100.00
   The viscosity of such antimycotic gels is normally about 250 000 to 400 000 mPa·s (RV20 rotational viscometer, M5 system, SV2 measuring unit, from Thermo Haake, at 0.45 s$^{-1}$, 20° C.).
   Formulation 6B corresponds to formulation 6A but contains no octenidine dihydrochloride.

7. Antimycotic Cream
   0.1 g octenidine dihydrochloride
   0.5 g clotrimazole
   0.6 g Cremophor A 25 (ceteareth-25)
   5.0 g Cutina GMS (glycerol stearate)
   10.0 g Eutanol G (octyldodecanol)
   8.0 g Lanette O (cetylstearyl alcohol)
   0.5 g silicone oil
   1.0 g phenoxyethanol
   4.0 g sorbitol
   water ad 100.00 g
   The viscosity of such creams is typically about 1000 to 2000 mPa·s (RV20 rotational viscometer, M5 system, SV2 measuring unit, from Thermo Haake, at 160 s$^{-1}$, 20° C.).

8. Vaginal Suppositories
   0.2 g octenidine dihydrochloride
   macrogol 1000 ad 100 g

EXAMPLE 2

Method

The bactericidal and fungicidal activity was determined in the quantitative suspension test with high protein loading ("dirty conditions") as specified in the standard methods of the Deutsche Gesellschaft für Hygiene and Mikrobiologie e.V. for testing chemical disinfection methods (date: 1 Sep. 2001). For methodological reasons, products ready for use can be tested only in concentrations of ≦80% by weight.

| Test organisms | |
| --- | --- |
| Staphylococcus aureus | ATCC 6538 |
| Pseudomonas aeruginosa | ATCC 15422 |
| Escherichia coli | ATCC 10538 |
| Enterococcus hirae | ATCC 10541 |
| Candida albicans | ATCC 10231 |

2.1 Quantitative Suspension Test with High Protein Loading (RF Values) with Formulation 1 (Gel)

| | 1 min | 5 min | 15 min |
| --- | --- | --- | --- |
| S. aureus | | | |
| 80 wt. % | ≧6.32 | ≧6.31 | ≧6.27 |
| 50 wt. % | ≧6.32 | ≧6.31 | ≧6.27 |
| P. aeruginosa | | | |
| 80 wt. % | ≧6.1 | ≧6.15 | ≧6.12 |
| 50 wt. % | 0 | 2.10 | 5.52 |
| E. coli | | | |
| 80 wt. % | ≧6.03 | ≧6.12 | ≧6.08 |
| 50 wt. % | ≧6.03 | ≧6.12 | ≧6.08 |
| E. hirae | | | |
| 80 wt. % | ≧6.12 | ≧6.12 | ≧6.08 |
| 50 wt. % | 5.82 | ≧6.12 | ≧6.08 |
| C. albicans | | | |
| 80 wt. % | ≧5.67 | ≧5.46 | ≧5.43 |
| 50 wt. % | 2.17 | 3.94 | ≧5.43 |

This formulation is a wound gel for wound treatment with rapid activity and a high proportion of humectant factors as required in the context of moist wound treatment. The results show that the gel ready for use has sufficient activity against all test organisms after acting for only 1 minute even with high protein loading.

2.2 Quantitative Suspension Tests with Formulation 3 (O/W Cream)

10 g of formulation 3 were weighed out and mixed with 0.1 ml of suspensions of Staph. aur. and Staph. epidermidis microbes. A glass rod was used to incorporate the microbe suspension thoroughly into the cream in order to achieve good and uniform distribution. After 6 hours, 1 g of cream was removed in each case and thoroughly stirred with 9 ml of neutralizer solution. After the neutralizer had acted for 20 minutes, 0.1 ml was removed and transferred with a spatula to an agar plate with casein, soya peptone agar.

Result:

|  | Formulation 3 | | Placebo formulation 3 | |
|---|---|---|---|---|
| Microbe | Sample 1 | Sample 2 | Sample 1 | Sample 2 |
| Staph. aur. | 0 CFU | 0 CFU | Lawn growth | Lawn growth |
| Staph. epid. | 0 CFU | 0 CFU | Lawn growth | Lawn growth |

Formulation 3 shows a complete effect, i.e. no colony-forming units (CFU) are to be found, whereas a lawn growth was to be found with the placebo owing to the absence of octenidine (placebo). Counting of CFUs was quite impossible.

2.3 Skin Tests with Formulation 3

For this purpose, 0.1 ml of a suspension of *Staph. epidermidis* microbes (skin tests with *Staph. aur*. are not permitted) was put on 5 cm² of forearm and allowed to dry. Subsequently, 0.1 g of formulation 3 was put on one forearm and 0.1 g of fucidin cream was put on the other. The cream was distributed well using a finger-stall and left to absorb. The treated places were then covered with a pad stuck in place with a transparent dressing (Tegaderm, from 3M). After 2 and 6 hours, the microbes still present were removed using a neutralizer solution by the ring method (d=3 cm). A further area of skin was treated with water and served as control. A mixture of Tween 80, saponin, histidine and cisteine was used as mobile composition.

|  | Action time | RF values |
|---|---|---|
| Formulation 3 | 2 hours | 2.72 |
| Formulation 3 | 6 hours | 2.91 |
| Fucidin cream | 2 hours | 1.63 |
| Fucidin cream | 6 hours | 2.09 |

Formulation 3 shows a better effect than fucidin cream both after 2 hours and after 6 hours.

Re Formulation 6

Method: Plate Diffusion Test

1. Agar Well Test
   Solutions and Nutrient Media:
   CSA (casein peptone-soya peptone agar)
   SA (Sabouraud's dextrose agar)
   CSL (casein peptone-soya peptone solution)
   NaCl (physiological saline, 0.85% by weight)
   Malt (beer wort-peptone agar)

Test Microbes:

| Staphylococcus aureus | ATCC 6538 |
|---|---|
| Pseudomonas aeruginosa | ATCC 15422 |
| Escherichia coli | ATCC 11229 |
| Candida albicans | ATCC 10231 |
| Aspergillus niger | ATCC 6275 |

Culturing and Preparation of the Inoculation Solutions:

| Bacteria: | 24-hour 10 ml CSL cultures are set up from 24-hour CS slant agar cultures. The titre of the bacterial suspensions is ~$10^9$ CFU/ml. |
|---|---|
| Yeasts: | 72-hour 10 ml CSL cultures are set up from 72-hour malt plate cultures. The titre of the yeast suspension is ~$10^8$ CFU/ml. |
| Moulds: | A 7- to 14-day old *A. niger* culture on Sabouraud's agar is rinsed off with 5 ml of sterile NaCl solution, filtered through a sterile glass funnel with glass wool and made up to 100 ml. This is diluted 1:100 with sterile NaCl solution before use. The titre of the mould suspension is ~$10^6$ CFU/ml. |

Procedure:

0.1 ml of the bacterial suspension is transferred with a spatula to CSA.

0.1 ml of the *C. albicans* suspension is transferred with a spatula to SA.

0.2 ml of the *A. niger* suspension is transferred with a spatula to SA.

A hole 9 mm in diameter is cut with a flame-sterilized cork borer in the middle of the agar plates. This hole is filled to the top with the product to be tested. The plates are left to stand at room temperature for prediffusion for 2 hours.

Bacteria and yeasts are incubated at 36° C. for 24 to 48 hours. The moulds are incubated at 25° C. for 3 days.

Evaluations:

The zone of inhibition is measured from the edge of the hole to the start of microbe growth. The result is stated in mm. If the microbe has grown to the edge of the hole, the zone of inhibition=0 mm.

| Results 0.1 ml of microbe suspension was transferred by spatula 0.15 g of gel weighed out per hole | | |
|---|---|---|
|  | 6A | 6B |
| *Staph. aureus* | 5 | 5 |
| *E. coli* | 2 | 0 |
| *Pseud. aerug.* | 3 | 2.5 |
| *Proteus mirabilis* | 2.5 | 0 |
| *Strept. Faecium* | 6 | 6 |
| *Candida albicans* | 5 | 6 |
| *Trichophyton mentagrophytes* | 20.7 | 20.0 |
| *Trirubum* | 15.0 | 7.3 |
| *Microsporum gypseum* | 22.7 | 17.3 |
| *Epidermophyton floccosum* | 35.0 | 34.7 |
| *Aspergillus niger* | 11.7 | 10.0 |
| *Penicillium furnicolosum* | 10.3 | 10.0 |

The invention claimed is:

1. A semisolid pharmaceutical composition for the treatment of wounds, atopic dermatitides, infected eczemas, dermatomycoses, vaginal infections, acne, herpes and/or for controlling multidrug-resistant pathogens, comprising:

octenidine dihydrochloride in an amount from 0.005 to 5% by weight;
propylene glycol;
hydroxyethylcellulose; and
water.

2. The composition according to claim 1, wherein the amount of octenidine dihydrochloride is from 0.01 to 2% by weight.

3. The composition according to claim 1, wherein the composition is in a form selected from the group consisting of a gel, an O/W cream, W/O cream, O/W/O cream, W/O/W cream, ambiphilic cream, ointment and a suppository.

4. The composition according to claim 3, wherein the composition is a topical composition.

5. The composition according to claim 2, wherein the amount of octenidine dihydrochloride is from 0.02 to 1% by weight.

6. The composition according to claim 5, wherein the amount of octenidine dihydrochloride is from 0.03 to 0.8% by weight.

7. The composition according to claim 6, wherein the amount of octenidine dihydrochloride is form 0.05 to 0.5% by weight.

* * * * *